(12) United States Patent
Babish et al.

(10) Patent No.: US 6,908,630 B2
(45) Date of Patent: Jun. 21, 2005

(54) COMBINATIONS OF SESQUITERPENE LACTONES AND DITEPENE TRIEPOXIDE LACTONES FOR SYNERGISTIC INHIBITION OF CYCLOOXYGENASE-2

(75) Inventors: John G. Babish, Brooktondale, NY (US); Terrence Howell, Dryden, NY (US); Linda Pacioretty, Brooktondale, NY (US)

(73) Assignee: Metaproteomics, LLC, San Clemente, CA (US)

( * ) Notice: Subject to any disclaimer, the term of this patent is extended or adjusted under 35 U.S.C. 154(b) by 125 days.

(21) Appl. No.: 09/919,349

(22) Filed: Jul. 31, 2001

(65) Prior Publication Data

US 2002/0077299 A1 Jun. 20, 2002

Related U.S. Application Data
(60) Provisional application No. 60/222,167, filed on Aug. 1, 2000.

(51) Int. Cl.$^7$ .................. A61K 35/78; A01N 43/16; A01N 43/08

(52) U.S. Cl. .................. 424/725; 514/453; 514/468

(58) Field of Search .................. 424/725, 439; 514/453, 468, 825, 863, 914, 175, 846

(56) References Cited

U.S. PATENT DOCUMENTS

| | | | |
|---|---|---|---|
| 5,500,340 | A | 3/1996 | Lipsky et al. |
| 5,962,516 | A | 10/1999 | Qi et al. |
| 6,271,213 | B1 * | 8/2001 | Henderson et al. |
| 6,333,304 | B1 * | 12/2001 | Bath et al. |
| 6,346,519 | B1 * | 2/2002 | Petrus |

FOREIGN PATENT DOCUMENTS

| | | | |
|---|---|---|---|
| DE | 4212122 A1 | * | 10/1993 |
| JP | 07033668 A | * | 2/1995 |

OTHER PUBLICATIONS

Tao et al. Arthritis & Rheumatism (Jan. 1998), vol. 41(1): 130–138. Effects of Tripterygium wilfordii Hook F extracts on induction of cyclooxygenase 2 activity and prostaglandin E2 production.*

Hwang et al. Biochemical & Biophysical Research Communications (1996), vol. 226(3): 810–818. Inhibition of the expression of inducible cyclooxygenase and proinflammatory cytokines by sesquiterpene lactones in macrophages correlates with the inhibition of.*

H. Sumner, U. Salan, D. W. Knight and J.R.S. Hoult—Inhibition of 5-Lipoxygenase and Cyclo-Osygenase in Leukocytes by Feverfew (Involvement of Sesquiterpene Lactones and Other Components). *Biochem. Pharmacol.* 1992: 43(11):2313–20.

W. A. Groenwegen, D. W. Knight, S. Heptinstall—Compounds Extracted from feverfew that have Anti–secretory Activity contain an α–methylene Butyrolactone Unit—*J. Pharm Pharmacol.* 1986 38(9):709–12.

V. J. Pugh, K. Sambo, *J. Pharm. Pharmacol.* 1988 40(10):743–5—Prostaglandin Synthetase Inhibitors in Feverfew.

Tournier, et al. Effect of the Chloroform Extract of Tanacetum vulg. Feb. 1999;51(2):215–9 vol. 51 *J. Pharm. Pharmacol.*

Hehner, et al. The Antiinflammatory Sequiterpene Lactone Parthen Nov. 15, 1999; 163(10):5617–23 vol. 163 *J. Immunol.*

H. R. Wong and I. Y. Menendez—Seswquiterpene Lactones Inhibit Inductible Nitric Oxide Synthase Gene Expression in Cultured Rat Aortic Smooth Muscle Cells—*Biochem. Biophys. Res. Commun.* 1999 27:262(2):375–80.

Lopes Vaz, A., Double–blind Clinical Evaluation of the Relative Efficacy of Ibuprofen and Glucosamine Sulphate in the Management of Osteoarthritis of the Knee in Outpatients, 8 *Curr. Med Res Opin.* 145–149 (1982).

P. K. Smith, R.I. Krohn, G.T. Hermanson, A.K. Mallia, etc.—Measurement of Protein Using Bicinchoninic Acid. *Anal. Biochem.* 1985 (150(1):76–85.

Noreen, Y., et al. (*J. Nat. Prod.* 61, 2–7, 1998) Development of a Radiochemical Cyclooxygenase–1 and –2 in Vitro Assay for Indentification of Natural Products as Inhibitors of Prostaglandin Biosynthesis (The ability of a Test Material to Inhibit COX–1 Synthesis of PGE2.).

Hamberg, M. and Samuelsson, B. (*J. Biol. Chem.* 1971, 246,6713–6721) On the Metabolism of Prostaglandins E1 and E2 in Man (Determination of PGE2 Concentration in Medium).

T. C. Chou and P. Talaly—Median Effect Methods Described (*Trends Pharmacol. Sci.* 4:450–454).

T–C Chou and P. Talalay—A Simple Generalized Equation for the Analysis of Multiple Inhibitions of Michaelis–Menten Kinetic Systems—*Journal of Biological Chemistry*, vol. 252. No. 18, 6438–6442, 1977.

P. M. Bork, M. Lienhard Schmitz, M. Kuhnt, etc.—Sesquiterpene Lactone Containing Mexican Indian Medicinal Plants and Pure Sesquiterpene Lactones as Potent Inhibitors of Transcription Factor NF—B—*FEBS Letters* 1997 27: 402(1):85–90.

(Continued)

*Primary Examiner*—Christopher R. Tate
*Assistant Examiner*—Michele C. Flood
(74) *Attorney, Agent, or Firm*—McDermott, Will & Emery

(57) ABSTRACT

A novel formulation is provided that serves to inhibit the inflammatory response in animals. The formulation comprises, as a first component an effective amount of a diterpene triepoxide lactone species and an effective amount of a second component of a sesquiterpene lactone species or derivatives thereof, and provides synergistic anti-inflammatory effects in response to physical or chemical injury or abnormal immune stimulation due to a biological agent or unknown etiology.

25 Claims, 4 Drawing Sheets

OTHER PUBLICATIONS

X Tao, J J Cai and P E Lipsky—The identity of Immunosuppressive Components of the Ethyl Acetate Extract and Chloroform Methanol Extract (T2) of Tripterygium Wilfordii Hook. F *Journal of Pharmacology and Experimental Therapeutics* 1995 272:1305–1312.

H Towbin, T Staehelin and J Gordon—Electrophoretic Transfer of Proteins from Polyacrylamide gets to Nitrocellulose Sheets; Procedure and some Applications—*Proc. Natl. Acad. Sci. USA* vol. 76, No. 9, pp 4350–4554, 1979.

U K Laemmli and M Favre—Maturation of the Head of Bacteriophage T4 1. DNA Packaging Events—*J. Mol. Biol.* (1973) 80, 575–599.

* cited by examiner

DITERPENE TRIEPOXIDE LACTONE

TRIPTOLIDE

*DITERPENE TRIEPOXIDE LACTONE*

*PARTENOLIDE*

COMBINATIONS OF SESQUITERPENE LACTONES AND DITEPENE TRIEPOXIDE LACTONES FOR SYNERGISTIC INHIBITION OF CYCLOOXYGENASE-2

RELATED APPLICATIONS AND PRIORITY CLAIM

This application claims the benefit of U.S. Provisional Application No.60/222,167 filed Aug. 1, 2000.

FIELD OF THE INVENTION

The present invention relates generally to a composition exhibiting synergistic inhibition of the expression and/or activity of inducible cyclooxygenase-2 (COX-2). More particularly, the composition comprises a combination of a diterpene triepoxide lactone species and a sesquiterpene lactone species or derivatives thereof. The composition functions synergistically to the activities of the individual components, i.e., inhibiting the inducibility and/or activity of inducible cyclooxygenase (COX-2) with no significant effect on constitutive cyclooxygenase (COX-1).

BACKGROUND OF THE INVENTION

Inflammatory diseases affect more than fifty million Americans. As a result of basic research in molecular and cellular immunology over the last ten to fifteen years, approaches to diagnosing, treating and preventing these immunologically-based diseases has been dramatically altered. One example of this is the discovery of an inducible form of the cyclooxygenase enzyme. Constitutive cyclooxygenase (COX), first purified in 1976 and cloned in 1988, functions in the synthesis of prostaglandins (PGs) from arachidonic acid (AA). Three years after its purification, an inducible enzyme with COX activity was identified and given the name COX-2, while constitutive COX was termed COX-1.

COX-2 gene expression is under the control of pro-inflammatory cytokines and growth factors. Thus, the inference is that COX-2 functions in both inflammation and control of cell growth. While COX-2 is inducible in many tissues, it is present constitutively in the brain and spinal cord, where it may function in nerve transmission for pain and fever. The two isoforms of COX are nearly identical in structure but have important differences in substrate and inhibitor selectivity and in their intracellular locations. Protective PGs, which preserve the integrity of the stomach lining and maintain normal renal function in a compromised kidney, are synthesized by COX-1. On the other hand, PGs synthesized by COX-2 in immune cells are central to the inflammatory process.

The discovery of COX-2 has made possible the design of drugs that reduce inflammation without removing the protective PGs in the stomach and kidney made by COX-1. These selective COX-2 inhibitors may not only be anti-inflammatory, but may also be actively beneficial in the prevention and treatment of colon cancer and Alzheimer's disease.

An ideal formulation for the treatment of inflammation would inhibit the induction and activity of COX-2 without affecting the activity of COX-1. Historically, the non-steroidal and steroidal anti-inflammatory drugs used for treatment of inflammation lack the specificity of inhibiting COX-2 without affecting COX-1. Therefore, most anti-inflammatory drugs damage the gastrointestinal system when used for extended periods. Thus, new treatments for inflammation and inflammation-based diseases are urgently needed.

The natural pharmacopoeia of plants and herbs used in traditional medicines for the treatment of inflammatory conditions was recently found to contain COX-2 inhibitors. One such plant is *Triptergium wilfordi* (TW). This herb, known as Lei Gong Teng in China, has been used to treat patients suffering with rheumatoid arthritis with a 92% efficacy rate. Lei Gong Teng is available in the U.S. and is advertised to support the healthy functioning of bone joints (www.China-Med.net).

Over 60 compounds have been isolated from TW, and many have been identified as having anti-inflammatory and immunosuppressive activity. Representative compounds that have been isolated from TW include triptolide, 16-hydroxytriptolide, triptophenolide, tripdiolide, and celastrol. However, the administration and therapeutic effectiveness of these compounds have generally been limited by their low margins of safety.

Triptolide is one of the active, nonalkaloid principles isolated from TW and possesses an extensive suppressive effect on immune function, especially on T and B lymphocytes. Structurally, triptolide is a member of the group of diterpene triepoxide lactones (FIG. 1). The inhibitory effect is direct and believed to occur through the inhibition of interluken-2 (IL-2) production and IL-2R (receptor) expression (Tao, et al. (1995) J. Pharmacol. Exp. Therap. 272:1305; U.S. Pat. No. 5,500,340 to Lipsky et al. Mar. 19, 1996). Clinical trials show that it significantly inhibits the proliferation of peripheral blood mononuclear cells of rheumatic arthritis patients. After receiving this medication, patients usually indicate that stiffness, walking, and hand strength are improved with a decrease in inflammation index. Although not generally life-threatening, adverse effects of triptolide are relatively common in the clinical setting. Approximately 28% of patients taking this compound show some type of side effects, such as gastrointestinal disturbance, nausea and vomiting, hypotension and edema.

Therefore, while triptolide may be useful as an anti-inflammatory agent, it can be toxic even in clinically effective doses. Other researchers have used the triptolide molecule as a starting point for the synthesis of novel analogs expressing similar immune effects, while exhibiting lower toxicity (U.S. Pat. No. 5,962,516 to Qi et al. Oct. 5, 1999). Rather than modifying the triptolide molecule to achieve greater efficacy and lower toxicity, it is the object of this invention to combine triptolide, or a representative diterpene epoxide lactone, with a second molecule to produce a synergistic effect in the target cell. One such synergistic response would be the inhibition of inducible COX-2.

Leaves or infusions of feverfew, *Tanacetum parthenium*, have long been used as a folk remedy for the relief of fever, arthritis and migraine headaches. Previous reports using feverfew extracts have suggested interference with arachidonate metabolism as the mechanism behind these pharmacological effects. In one study (Sumner et al. (1992) Biochem. Pharmacol. 43:2313–2320), crude chloroform extracts of fresh feverfew leaves produced dose-dependent inhibition of the generation of thromboxane B2 and leukotriene B4 by ionophore- and chemoattractant-stimulated rat peritoneal leukocytes and human polymorphonuclear leukocytes. Other research has suggested inhibition of platelet aggregation and the platelet release reaction by feverfew extracts (Groenewegen et al. (1986) J. Pharm. Pharmacol. 38:709–712). Numerous publications suggest that the biologically active components of feverfew are sesquiterpene lactones, with parthenolide being the most abundant.

In the literature approximately 25, separate biological effects have been reported for parthenolide. The potential pharmacological activities range from the inhibition of isolated bovine prostaglandin synthetase (Pugh and Sambo (1988) J. Pharm. Pharmacol. 40:743–745) to the prevention of ethanol-induced gastric ulcers in the rat (Tournier et al. (1999) J. Pharm. Pharmacol. 51:215–219). Research at the molecular level has described parthenolide inhibition of nuclear factor kappa B (NF-kB) activation in several cell-based systems (Hehner et al. (1999) J. Immunol. 163:5617–5623; Bork et al. (1997) FEBS Letters 402:85–90) and inhibition of inducibile nitric oxide gene expression in cultured rat aortic smooth muscle cells (Wong and Menendez (1999) Biochem. Biophys. Res. Commun. 262:375–380). While these molecular events may account, in part, for some of the biological actions of parthenolide, there exists no consensus on the exact nature of the underlying mechanism for its anti-inflammatory effects.

Clinically effective doses of parthenolide for migraine prevention are on the order of micrograms per kg body weight daily. Human clinical trials have verified the minimum effective dose for migraine prevention, as well as the associated discomfort of nausea and vomiting associated with use of 125 mg of feverfew extract per day. The feverfew extracts used in these trials generally contained between 0.2 to 0.7 percent parthenolide. Therefore, the minimally effective dose of parthenolide would be estimated to be approximately 250 micrograms per day or 4 micrograms parthenolide per kg body weight. Commercial, standardized preparations of feverfew deliver between 600 to 4000 micrograms parthenolide per daily dose. While more than sufficient to effectively control migraine frequency, it is doubtful that these doses of parthenolide would be sufficient to address inflammatory responses.

Research literature on the in vitro anti-inflammatory effects of parthenolide reports inhibitory constants in the micromolar range. Assuming a volume of distribution greater than several hundred mL per kg and a median resonance time less than 12 hours, these parthenolide concentrations could only be achieved and maintained in vivo with dosing mg amounts of parthenolide per kg bodyweight. While such dosing studies have been performed successfully in laboratory animals, no clinical reports describe similar doses of parthenolide in humans. Based upon these estimates, a clinically successful preparation of parthenolide for inflammatory conditions would be required to deliver at least 15 mg parthenolide/kg-day. However, such relatively high doses of parthenolide would be commercially prohibitive due to the cost of production, even for a therapeutic formulation.

Combinations of botanicals containing triptolide along with other herbs have been use in both traditional and commercial medicine. However, the triptolide content of TW is only 0.1%, leaving 99.9% of the ingredients of TW as undefined. Such a large unknown fraction makes it extremely unlikely that triptolide is a significant factor in the pharmacological response of TW in this formulation. Thus, it would be useful to identify a compound that would specifically enhance the anti-inflammatory effect of triptolide so that it could be used at sufficiently low doses or at current clinical doses with no adverse side effects. The optimal formulation of triptolide for preserving the health of joint tissues, for treating arthritis or other inflammatory conditions has not yet been discovered. A formulation combining triptolide and parthenolide to synergistically inhibit COX-2 and support the normalization of joint function has not yet been described or discovered.

While glucosamine is generally accepted as being effective and safe for treating osteoarthritis, medical intervention into the treatment of degenerative joint diseases is generally restricted to the alleviation of its acute symptoms. Medical doctors generally utilize non-steroidal and steroidal anti-inflammatory drugs for treatment of osteoarthritis. These drugs, however, are not well-adapted for long-term therapy because they not only lack the ability to promote and protect cartilage, they can actually lead to degeneration of cartilage or reduction of its synthesis. Moreover, most non-steroidal, anti-inflammatory drugs damage the gastrointestinal system when used for extended periods. Thus, new treatments for arthritis are urgently needed.

The joint-protective properties of glucosamine would make it an attractive therapeutic agent for osteoarthritis except for two drawbacks: (i) the rate of response to glucosamine treatment is slower than for treatment with anti-inflammatory drugs, and (ii) glucosamine may fail to fulfill the expectation of degenerative remission. In studies comparing glucosamine with non-steroidal anti inflammatory agents, for example, a double-blinded study comparing 1500 mg glucosamine sulfate per day with 1200 mg ibuprofen, demonstrated that pain scores decreased faster during the first two weeks in the ibuprofen patients than in the glucosamine-treated patients. However, the reduction in pain scores continued throughout the trial period in patients receiving glucosamine and the difference between the two groups turned significantly in favor of glucosamine by week eight. Lopes Vaz, A., Double-blind clinical evaluation of the relative efficacy of ibuprofen and glucosamine sulphate in the management of osteoarthritis of the knee in outpatients, 8 Curr. Med Res Opin. 145–149 (1982). Thus, glucosamine may relieve the pain and inflammation of arthritis at a slower rate than the available anti-inflammatory drugs.

An ideal formulation for the normalization of cartilage metabolism or treatment of osteoarthritis would provide adequate chondroprotection with potent anti-inflammatory activity. The optimal dietary supplement for osteoarthritis should enhance the general joint rebuilding qualities offered by glucosamine and attenuate the inflammatory response without introducing any harmful side effects. It should be inexpensively manufactured and comply with all governmental regulations.

However, the currently available glucosamine formulations have not been formulated to optimally attack and alleviate the underlying causes of osteoarthritis and rheumatoid arthritis. Moreover, as with many commercially-available herbal and dietary supplements, the available formulations do not have a history of usage, nor controlled clinical testing, which might ensure their safety and efficacy.

It would be useful to provide a composition that would specifically and synergistically enhance the anti-inflammatory effect of triptolide so that these could be used at sufficiently low doses or at current clinical doses with no adverse side effects.

SUMMARY OF THE INVENTION

The present invention provides a composition comprising a diterpene triepoxide lactone species and a sesquiterpene lactone species that specifically and synergistically enhance the anti-inflammatory effect of the diterpene triepoxide lactone species or the sesquiterpene lactone species. Any diterpene triepoxide lactone or sesquiterpene lactone species is inclusive of derivatives of the respective genus. However, additional species or mixtures of species within the various genera may be present in the composition which is limited in scope only by the combinations of species within the various genera that exhibit the claimed synergistic functionality.

The composition functions synergistically to inhibit the inducibility and/or activity of COX-2 with no effect on COX-1.

The present invention further provides a composition of matter to increase the rate at which glucosamine or chondrotin sulfate function to normalize joint movement or reduce the symptoms of osteoarthritis.

One specific embodiment of the present invention is a composition comprising an effective amount of triptolide and parthenolide, which functions synergistically to the activities of the individual components.

The present invention further provides is a method of dietary supplementation and a method of treating inflammation or inflammation-based diseases in a warm-blooded animal which comprises providing to the animal suffering symptoms of inflammation the composition of the present invention which specifically and synergistically enhances the anti-inflammatory effect of a diterpene triepoxide lactone, or a sesquiterpene lactone, and continuing to administer such a dietary supplementation of the composition until said symptoms are eliminated or reduced.

DETAILED DESCRIPTION OF THE INVENTION

Figure 1A:
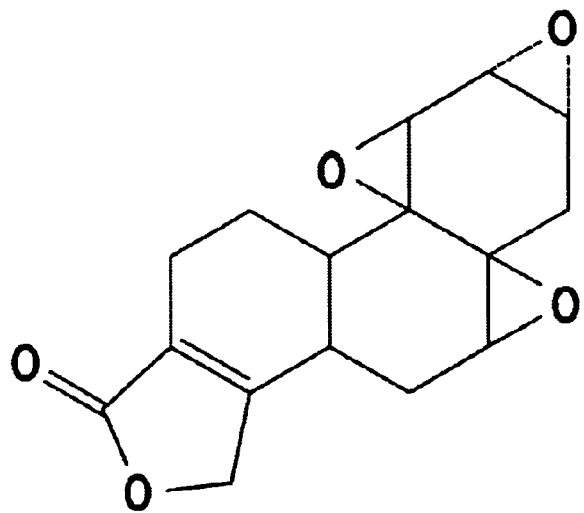
FIG. 1 illustrates the general chemical structure of [A1] the diterpene triepoxide lactone genus and [A2] triptolide as a species within that genus.

Before the present composition and methods of making and using thereof are disclosed and described, it is to be understood that this invention is not limited to the particular configurations, as process steps, and materials may vary somewhat. It is also intended to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

The present invention provides a composition having a synergistic inhibitory effect on the expression and/or activity of COX-2. More particularly, the composition comprises an active diterpene triepoxide lactone and an active sesquiterpene lactone or derivatives thereof. Preferably, the molar ratio of the active diterpene triepoxide lactone and active sesquiterpene lactone or derivatives thereof is within a range of 1:1 to 1:10, and more preferably within a range of 1:2.5 to 1:10. The composition provided by the present invention can be formulated as a dietary supplement or therapeutic composition. The composition functions synergistically to inhibit the inducibility and/or activity of COX-2 with little or no effect on COX-1.

As used herein, the term "dietary supplement" refers to compositions consumed to affect structural or functional changes in physiology. The term "therapeutic composition" refers to any compounds administered to treat or prevent a disease.

As used herein, the term "active sesquiterpene lactone" or "active diterpene triepoxide lactone" refers to a species within the sesquiterpene lactone or diterpene triepoxide lactone genera that is capable of inhibiting the inducibility and/or activity of COX-2 while having no significant effect on COX-1 or is capable of inhibiting or reducing the severity of a severe inflammatory response. All active sequesterpene lactone species have an α-methylene or γ-lactone functional group and are capable of inhibiting or reducing the severity of an inflammatory response.

As used herein, diterpene triepoxide lactones, sesquiterpenes lactones or "derivative" thereof refers to compounds or their naturally occurring or synthetic derivatives of species within the scope of the respective genera. Representative species within each genus are listed in Table 1. Of the species listed under each genus in Table 1, those containing at least one asterisk (*) are preferred and those containing two asterisks (**) are particularly preferred.

TABLE 1

| DITERPENE TRIEPOSIDES LACTONES | ACTIVE SESQUITERPENE LACTONES |
|---|---|
| Tripchlorolide* | 5-α-Hydroxy-dehydrocostuslacone |
| Tripdiolide* | Burrodin* |
| Triptolide** | Chlorochrymorin |
| Triptonide** | Chrysandiol |
|  | Chrysartemin A |
|  | Chrysartermin B |
|  | Cinerenin |
|  | Confertiflorin* |
|  | Costunolide* |
|  | Curcolone |
|  | Cynaropicrin |
|  | Dehydrocostus lactone |
|  | Dehydroleucodin |
|  | Dehydrozaluzanin C |
|  | Deoxylactucin |
|  | Encelin** |
|  | Enhydrin** |
|  | Eremanthine |
|  | Eupaformonin |
|  | Eupaformosanin |
|  | Eupatolide |
|  | Furanodienone |
|  | Helenalin* |
|  | Heterogorgiolide |
|  | Lactucin |
|  | Leucanthin B** |
|  | Magnolialide |
|  | Melapomdin A** |
|  | Michelenolide |
|  | Parthenolide** |
|  | Psilostachyin A* |
|  | Repin |

"Conjugates" of diterpene triepoxide lactones, sesquiterpenes lactones or derivatives thereof means diterpene triepoxide lactones, or sesquiterpenes lactones covalently bound or conjugated to a member selected from the group consisting of mono- or di-saccharides, amino acids, sulfates, succinate, acetate and glutathione. Preferably, the mono- or di-saccharides is a member selected from the group consisting of glucose, mannose, ribose, galactose, rhamnose, arabinose, maltose, and fructose.

Therefore, one preferred embodiment of the present invention is a composition comprises a combination of an effective amount of parthenolide and triptolide. The resulting formulation of these combination functions to synergistically inhibit the inducibility and/or activity of COX-2 while showing little or no effect on COX-1. Therefore, the composition of the present invention essentially eliminates the inflammatory response rapidly without introducing any harmful side effects.

Figure 1B:
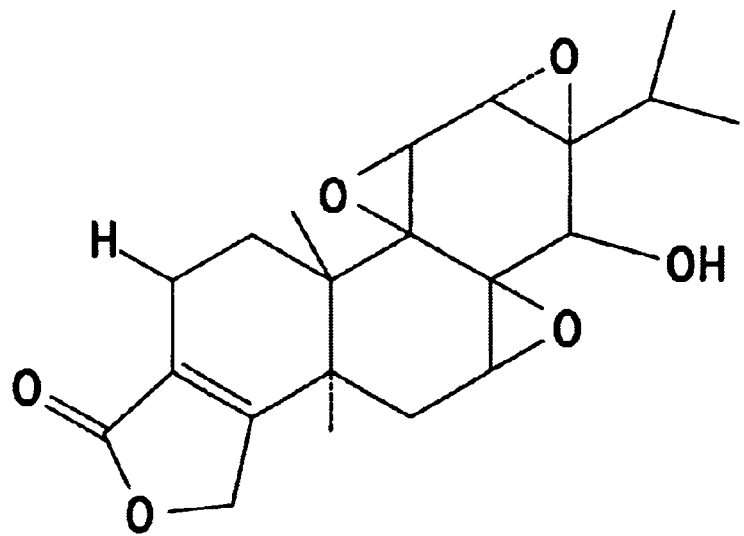

Preferably, the diterpene triepoxide lactones or triptolide (FIG. 1 [A1] and [A2]) employed in the present invention is a pharmaceutical grade botanical extract such as can be obtained commercially, for example, from Folexco Flavor Ingredients, 150 Domorah Drive, Montogomeryville, Pa. 18936. The triptolide used can be readily obtained from *Triptergium wilfordiim*. Pharmaceutical grade triptolide extract is standardized to have a triptolide content of greater than 50 percent. Additionally, it contains no alkaloids or glycosides normally found with triptolide generally isolated from botanical sources. The pharmaceutical, botanical grade extract must pass extensive safety and efficacy procedures. As employed in the practice of the present invention, the extract has a minimum triptolide content of about 1 to 50 percent by weight. Preferably, the minimum triptolide content is about 1 percent by weight. Alternatively, the triptolide may be synthesized using standard techniques known in chemical synthesis.

Figure 2A:
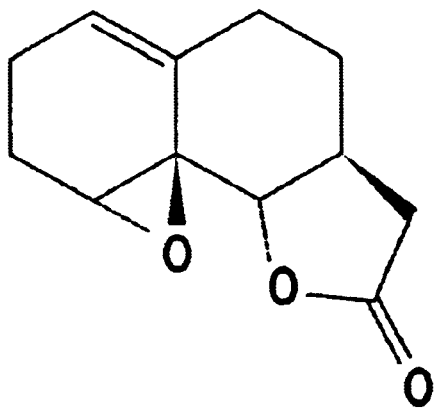
FIG. 2, [A1] and [A2] respectively, illustrates the general chemical structures of the sequuiterpene lactone genus and parthenolide as a species within that genus.
Figure 2B:
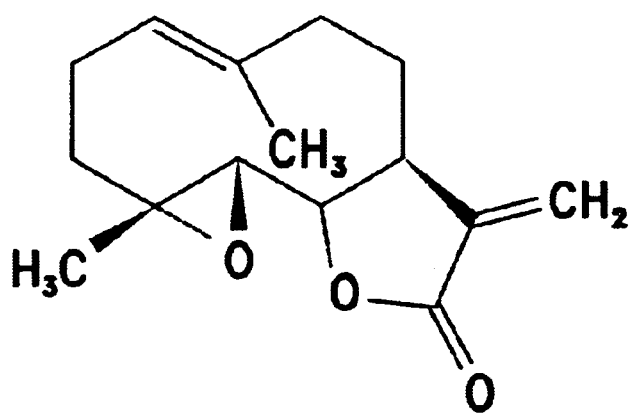

The sesquiterpene lactone genus, as represented by FIG. 2, [A1], and specifically the species parthenolide as represented by FIG. 2, [A2] is preferably a pharmaceutical grade preparation such as can be obtained from Folexco Flavor Ingredients, 150 Domorah Drive, Montogomeryville, Pa. 18936. The pharmaceutical grade extract must pass extensive safety and efficacy procedures. *Chrysanthemum parthenium* or *Tanacetum vulgare* serve as ready sources of parthenolide. Pharmaceutical grade parthenolide extract is greater than 5 weight percent. As employed in the practice of the invention, the extract has a parthenolide content of about 5 to 95 percent by weight. Preferably, the minimum parthenolide content is greater than 50 percent by weight. Without limiting the invention, it is anticipated that parthenolide would act to prevent an increase in the rate of transcription of the COX-2 gene by the transcriptional regulatory factor NF-kappa B.

The essence of the present invention is that, rather than modifying the diterpene triepoxide lactone or active sesquiterpene lactone molecules to achieve greater efficacy and lower toxicity, a second component is added that acts in a synergistic manner. Therefore, this invention relates to the discovery that when combining diterpene triepoxide lactones and an active sesquiterpene lactone or derivatives thereof, the combination produces a synergistic effect of the activities of the individual components in the target cell. One such synergistic response would be the specific inhibition of inducible COX-2.

It is discovered in the present invention that the combination of diterpene triepoxide lactones and an active sesquiterpene lactone provides for a synergistic effect on the activity of diterpene triepoxide lactones or an active sesquiterpene lactone. The result is a more selective effect on the activity of COX-2 at lower doses of diterpene triepoxide lactones or an active sesquiterpene lactone. By decreasing the dose of diterpene triepoxide lactones or an active sesquiterpene lactone to achieve the desired COX-2 inhibition, the probability of side effects from this compound decreases exponentially.

Preferably, a daily dose (mg/kg-day) of the present dietary supplement would be formulated to deliver, per kg body weight of the animal, about 0.001 to 3.0 mg diterpene triepoxide lactones and about 0.05 to 5 mg sesquiterpene lacotone. The composition of the present invention for topical application would contain one of the following: about 0.001 to 1 wt %, preferably 0.01 to 1 wt % diterpene triepoxide lactones or sesquiterpene lactones.

Additionally, the preferred composition of the present invention would produce serum concentrations in the following range: 0.01 to 10 nM diterpene triepoxide lactones, and 0.001 to 10 $\mu$M sesquiterpene lacotone.

Table 2 below provides a list of diseases in which COX-2 enzyme expression and activity may play a significant role and therefore are appropriate targets for normalization or treatment by the invention.

TABLE 2

| Disease | Tissue Affected |
| --- | --- |
| Addison's Disease | Adrenal |
| Allergies | Inflammatory cells |
| Alzheimer Disease | Nerve cells |
| Arthritis | Inflammatory cells |
| Atherosclerosis | Vessel wall |
| Colon Cancer | Intestine |
| Crohn's Disease | Intestine |
| Diabetes (type I)/type II | Pancreas |
| Eczema | Skin/Inflammatory cells |
| Graves' Disease | Thyroid |
| Guillain-Barre Syndrome | Nerve cells |
| Inflammatory Bowel Disease | Intestine |
| Leukemia | Immune cells |
| Lymphomas | Immune cells |
| Multiple Sclerosis | Nerve cells |
| Myasthenia Gravis | Neuromuscular junction |
| Osteoarthritis | Joint lining |
| Psoriasis | Skin |
| Primary Biliary Cirrhosis | Liver |
| Rheumatoid Arthritis | Joint lining |
| Solid Tumors | Various |
| Systemic Lupus Erythematosis | Multiple tissues |
| Uveitis | Eye |

In addition to the combination of diterpene triepoxide lactones and sesquiterpene lactones, the present composition for dietary application may include various additives such as other natural components of intermediary metabolism, vitamins and minerals, as well as inert ingredients such as talc and magnesium stearate that are standard excipients in the manufacture of tablets and capsules.

As used herein, "pharmaceutically acceptable carrier" includes any and all solvents, dispersion media, coatings, isotonic and absorption delaying agents, sweeteners and the like. These pharmaceutically acceptable carriers may be prepared from a wide range of materials including, but not limited to, diluents, binders and adhesives, lubricants, disintegrates, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. Except insofar as any conventional media or agent is incompatible with the active ingredients, its use in the present composition is contemplated. In one embodiment, talc and magnesium stearate are included in the present formulation. When these components are added they are preferably, the Astac Brand 400 USP talc powder and the veritable grade of magnesium stearate. Other ingredients known to affect the manufacture of this composition as a dietary bar or functional food can include flavorings, sugars, amino-sugars, proteins and/or modified starches, as well as fats and oils.

The dietary supplements, lotions or therapeutic compositions of the present invention can be formulated in any manner known by one of skill in the art. In one embodiment, the composition is formulated into a capsule or tablet using techniques available to one of skill in the art. In capsule or tablet form, the recommended daily dose for an adult human or animal would preferably be contained in one to six capsules or tablets. However, the present compositions may also be formulated in other convenient forms, such as an injectable solution or suspension, a spray solution or suspension, a lotion, gum, lozenge, food or snack item. Food, snack, gum or lozenge items can include any ingestable ingredient, including sweeteners, flavorings, oils, starches, proteins, fruits or fruit extracts, vegetables or vegetable extracts, grains, animal fats or proteins. Thus, the present compositions can be formulated into cereals, snack items such as chips, bars, gum drops, chewable candies or slowly dissolving lozenges.

The present invention contemplates treatment of all types of inflammation-based diseases, both acute and chronic. The present formulation reduces the inflammatory response and thereby promotes healing of, or prevents further damage to, the affected tissue. A pharmaceutically acceptable carrier may also be used in the present compositions and formulations.

According to the present invention, the animal may be a member selected from the group consisting of humans, non-human primates, such as dogs, cats, birds, horses, ruminants or other warm blooded animals. The invention is directed primarily to the treatment of human beings. Administration can be by any method available to the skilled artisan, for example, by oral, topical, transdermal, transmucosal, or parenteral routes.

The following examples are intended to illustrate but not in any way limit the invention:

EXAMPLE 1

Inhibition of Cyclooxygenase-2 Enzyme Expression in Human T Cells by Triptolide and Parthenolide This example hypothetically illustrates the effect of triptolide and parthenolide on COX-2 in cultured Jurkat cells. It is found that triptolide alone may decrease the expression of COX-2 protein in PMA stimulated cells and that parthenolide has little effect in the dose-range tested. In the presence of arachidonic acid (AA), the effectiveness of triptolide is markedly reduced. However, a combination of the two compounds exerted a powerful inhibition of the expression of COX-2 in the presence and absence of AA, with no observable signs of toxicity.

Chemicals: Anti-COX-2 antibodies may be purchased from Upstate Biotechnology (Lake Placid, N.Y.). Triptolide and parthenolide may be obtained from Sigma (St. Louis, Mo.). Arachidonic acid (AA), PMA and all other chemical may also be purchased from Sigma and are of the highest purity commercially available.

Human T cell lines: The Jurkat cell line is useful as a model for human T cells and may be obtained from the American Type Culture Collection (Bethesda, Md.). COX-2 is inducible in the Jurkat cell by PMA.

Cell plating: The Jurkat cells are propagated in suspension according to the instructions of the supplier. For experimentation, cells are seeded from a log-phase culture at a density of $1 \times 10^5$ cells per mL in 100 mm plates, 20 mL per plate, 3 plates per treatment. Serum concentration in the test medium is maintained at 0.5%. After 24 hours, the phytohemagglutinin (PHA) or PHA/AA combinations are added to the cell cultures, in 10 µL aliquots, to achieve effective concentrations.

Gel Electrophoresis: Sodium dodecyl sulfate polyacryamide gel electrophoresis (PAGE) is performed using 10% polyacrylamide gels as described by Laemmli, U. K. and Favre, M. (J. Mol. Biol. (1973) 80:575) with the modification that the cell lysates (100 µg/lane) are heated at 100 ° C. for three minutes.

Immunoblotting: The immunoblotting is performed as described by Tobin et al. (Proc. Nat. Acad. Sci. USA (1979) 76:4350), however, Milliblot SDE electroblot apparatus (Millipore, Bedford, Mass.) is used to transfer proteins from the polyacrylamide gels to an Immobilon® membrane filter. Complete transfers are accomplished in 25–30 minutes at 500 mA. Membranes used for blotting are blocked by incubating in TBS (Tris buffered saline, 50 mM Tris, 150 mM NaCl, pH 7.5) containing 5% nonfat dry milk for 30 minutes at room temperature. COX-2 protein is visualized by incubation of the blots with the anti-COX-2 antibody in TBST (0.5% Tween 20 in TBS) for two hours and then a second incubation at room temperature with alkaline phosphatase-conjugated secondary antibody diluted 1:1000 in TBST for two hours. The enzymatic reaction is developed for 15 minutes. The molecular weight of COX-2 is estimated by adding a molecular weight standard to reference lanes and staining the membrane filters with amido black 10B.

Blots are translated into TIFF-formatted files with a Microtech 600GS scanner and quantified using Scan Analysis (BIOSOFT, Cambridge, UK). Summary scans are then printed and peak heights are measured directly from the figure. One density unit (Du) is defined as one mm of the resulting peak height.

Protein determination: Spectrophotometric determination of protein concentration is determined with bicinchoninic acid as reported by Smith et al. (Anal. Biochem. (1985) 150:76).

Figure 3:
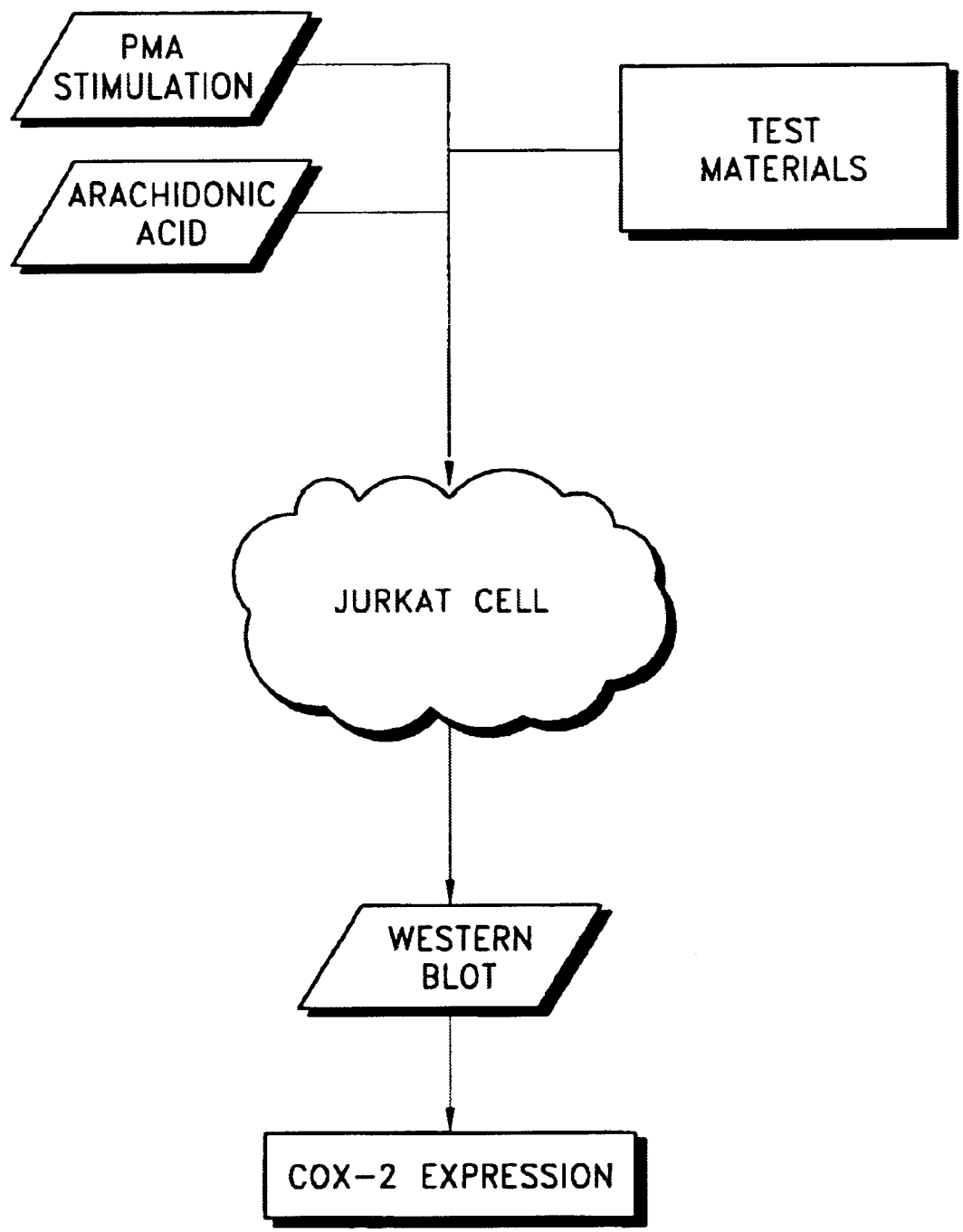
FIG. 3 provides a schematic for the experimental design of EXAMPLE 1.

FIG. 3 provides a schematic for the experimental design in which Jurkat cells are stimulated with PHA in the absence and present of arachidonic acid. Triptolide or parthenolide alone, or a combination of triptolide and parthenolide are added in a volume of 10 µL immediately to the medium immediately following the PHA treatment. Appropriate controls receive solvent only. Final concentrations of triptolide orparthenolide are 0, 0.01, 0.05, 0.1, 0.5, 1.0, 5.0 and 10 nM. For the mixtures, the first seven doses are simply combined. For example, the first dose of the combined treatment contains 0.01 nM triptolide and 0.01 nM oleanolic acid. Twenty-four hours after treatment, the cells are harvested, lysed and western blotting is done for the determination of COX-2 protein expression.

Figure 4:
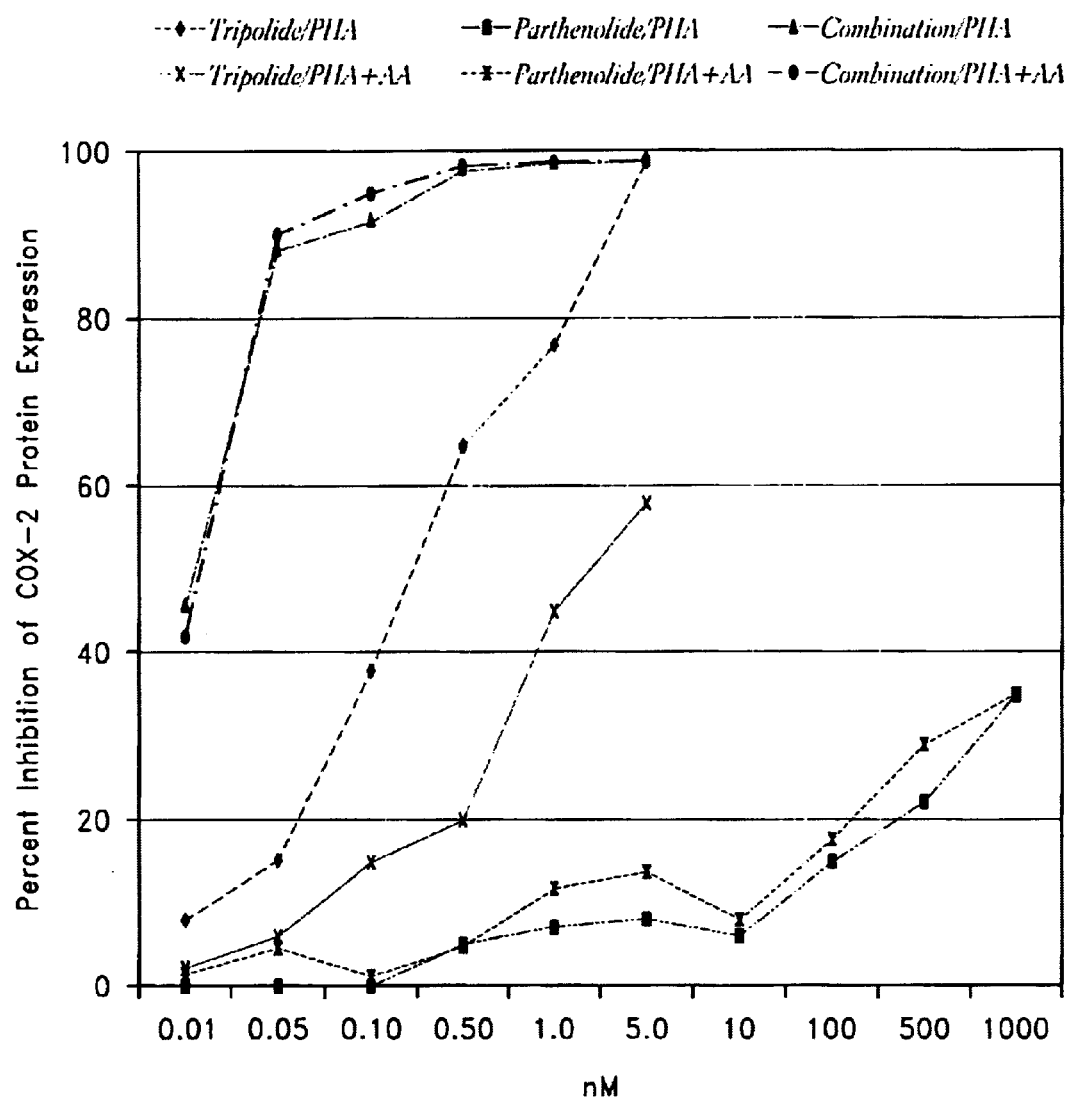
FIG. 4 is a line graph depicting the percent inhibition of COX-2 enzyme protein expression by individual and the combinations of the tested materials, as described in EXAMPLE 1, in the absence and presence of arachidonic acid (AA).

FIG. 4 is a line graph depicting the percent inhibition of COX-2 enzyme protein expression by triptolide, parthenolide and the combination of triptolide with parthenolide in the absence and presence of arachidonic acid. It is observed that triptolide functions to inhibit the expression of inducible cyclooxygenase 2 enzyme in the Jurkat cell line in the absence of arachidonic acid, and that this activity is enhanced more than 10-fold by parthenolide. Parthenolide alone does not inhibit COX-2 expression at physiologically relevant doses. In the presence of parthenolide, the inhibition of inducible COX-2 by triptolide is nearly complete, even at very low concentrations. In the presence of arachidonic acid, triptolide inhibition of COX-2 enzyme protein is compromised, but restored in the presence of parthenolide.

EXAMPLE 2

Normalization of Joint Functioning Following Trauma

A representative composition of the present invention as a dietary supplement would be in an oral formulation, i.e.

tablets, that would supply 0.01 mg triptolide/kg per day and 5.0 mg parthenolide/kg per day. Normalization of joint movement following physical trauma due to exercise or repetitive movement stress would be expected to occur following two to ten doses. This result would be expected in all animals.

EXAMPLE 3

Clinical Effectiveness of Lotion Formulations in the Treatment of Acne Rosacea A lotion designed to contain 0.1% wt triptolide and 0.1% parthenolide is applied to affected areas of patients who have exhibited acne rosace as diagnosed by their own practitioner and confirmed by an independent board-certified dermatologist. Self-evaluation tests and are administered one week prior to the study to quantify the surface area affected and redness. In addition, similar variables are scored by the professional clinical staff not aware of the patients treatment status. These evaluations are repeated on Days 0, 7, 14 and 21.

Patients are randomly assigned to the test formulation or a placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the combination composition of the present invention in a lotion formulation are considered improved if the patients' scores improve by greater than 20% from the pre-test scores within each category evaluated. The percentage of persons exhibiting improvement are compared between the combination formulations and the placebo control. The difference between the two groups is considered statistically significant if the probability of rejecting the null hypothesis when true is less than five percent.

EXAMPLE 4

Clinical Effectiveness of Lotion Formulations in the Treatment of Psoriasis

This example is performed in the same manner as described in the Example 3, except that the composition is applied to affected areas of patients who have exhibited psoriasis as diagnosed by their own practitioner and confirmed by an independent board-certified dermatologist. Self-evaluation tests are administered one week prior to the study to quantify the surface area affected and skin condition. In addition, similar variables are scored by the professional clinical staff not aware of the patients treatment status. These evaluations are repeated on Days 0, 7, 30 and 60.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the triptolide/parthenolide lotion formulation are considered improved if the patients' scores improve by greater than 20% from the pre-test scores within each category evaluated. The percentage of persons exhibiting improvement is compared between the triptolide/parthenolide formulation and the placebo control. The difference between the two groups is considered statistically significant if the probability of rejecting the null hypothesis when true is less than five percent.

EXAMPLE 5

Clinical Effectiveness of an Oral Formulation in the Treatment of Alzheimer's Disease An oral formulation as described in the Example 2 is administered to patients who have manifested an early stage of Alzheimer's Disease (AD), as diagnosed by their own practitioner and confirmed by an independent board-certified neurologist. Two weeks before the clinical trial, the patients undergo appropriate psychoneurological tests such as the Mini Mental Status Exam (MMSE), the Alzheimer Disease Assessment Scale (ADAS), the Boston Naming Test (BNT), and the Token Test (TT). Neuropsychological tests are repeated on Day 0, 6 weeks and 3 months of the clinical trial. The tests are performed by neuropsychologists who are not aware of the patient's treatment regimen.

Patients are randomly assigned to the test formulation or placebo at the start of the study. The test formulation and placebo are taken orally one or two times per day. Treatment for conditions such as diabetes, hypertension, etc. is allowed during the study. Scores are statistically compared between the test formulation and the placebo for each of the three observational periods. Without treatment, the natural course of AD is significant deterioration in the test scores during the course of the clinical trial. Patients treated with the triptolide/parthenolide formulation are considered improved if the patients' scores remain the same or improve during the course of the clinical trial.

EXAMPLE 6

Clinical Effectiveness of an Oral Formulation in the Treatment and Prevention of Colon Cancer An oral formulation as described in Example 2 is administered to patients who have manifested an early stage of colon cancer as diagnosed by their own practitioner and confirmed by a independent board-certified oncologist.

Patients are randomly assigned to the test formulation or placebo at the start of the study. The test formulation and placebo are taken orally one or two times per day. Treatment for conditions such as diabetes, hypertension, etc. is allowed during the study. Endoscopic evaluations are made at one, two, six and twelve months. Evidence of reappearance of the tumor during any one of the four follow-up clinical visits is considered a treatment failure. The percentage of treatment failures is compared between the triptolide/parthenolide formulation and the placebo control. The difference between the two groups is considered statistically significant if the probability of rejecting the null hypothesis when true is less than five percent.

EXAMPLE 7

Clinical Effectiveness of an Oral Formulation in the Treatment of Irritable Bowel Syndrome An oral formulation as described in Example 2 is administered to patients who have manifested irritable bowel syndrome as diagnosed by their practitioner. Normal bowel functioning is restored within 24 hours.

EXAMPLE 8

Normalization of Joint Functioning in Osteoarthritis

Using a composition described in Example 2, normalization of joint stiffness due to osteoarthritis occurs following five to twenty doses, in the presence or absence of glucosamine or chondroitin sulfate. In addition, the composition does not interfere with the normal joint rebuilding effects of these two proteoglycan constituents, unlike traditional non-steroidal anti-inflammatory agents.

EXAMPLE 9

Inhibition of COX-2 Enzyme Production of Prostaglandin E2 in Murine B Cells by Parthenolide and Triptolide This example illustrates the superior COX-2 inhibitory potency and selectivity of the combination of parthenolide and triptolide of the present invention compared to parthenolide or triptolide alone.

Inhibition of COX-2 Mediated Production of PGE2 in RAW 264.7 Cells

Equipment—balancer, analytical, Ohaus Explorer (Ohaus Model #EO1140, Switzerland), biosafety cabinet (Forma Model #F1214, Marietta, Ohio), pipettor, 100 to 1000 µL (VWR Catalog #4000-208, Rochester, N.Y.), cell hand tally counter (VWR Catalog #23609-102, Rochester, N.Y.), $CO_2$ incubator (Forma Model #F3210, Marietta, Ohio), hemacytometer (Hausser Model #1492, Horsham, Pa.), microscope, inverted (Leica Model #DM IL, Wetzlar, Germany), multi-channel pipettor, 12-Channel (VWR Catalog #53501-662, Rochester, N.Y.), Pipet Aid (VWR Catalog #53498-103, Rochester, N.Y.), Pipettor, 0.5 to 10 µL (VWR Catalog #4000-200, Rochester, N.Y.), pipettor, 100 to 1000 µL (VWR Catalog #4000-208, Rochester, N.Y.), pipettor, 2 to 20 µL (VWR Catalog #4000-202, Rochester, N.Y.), pipettor, 20 to 200 µL (VWR Catalog #4000-204, Rochester, N.Y.), PURELAB Plus Water Polishing System (U.S. Filter, Lowell, Mass.), refrigerator, 4° C. (Forma Model #F3775, Marietta, Ohio), vortex mixer (VWR Catalog #33994-306, Rochester, N.Y.), water bath (Shel Lab Model #1203, Cornelius, Oreg.).

Cells, Chemicals, Reagents and Buffers—Cell scrapers (Corning Catalog #3008, Corning, N.Y.), dimethylsulfoxide (DMSO) (VWR Catalog #5507, Rochester, N.Y.), Dulbecco's Modification of Eagle's Medium (DMEM) (Mediatech Catalog #10-013-CV, Herndon, Va.), fetal bovine serum, heat inactivated (FBS-HI) (Mediatech Catalog #35-011-CV, Herndon, Va.), lipopolysaccharide (LPS)(Sigma Catalog #L-2654, St. Louis, Mo.), microfuge tubes, 1.7 mL (VWR Catalog #20172-698, Rochester, N.Y.), penicillin/streptomycin (Mediatech Catalog #30-001-CI, Herndon, Va.), pipettips for 0.5 to 10 µL pipettor (VWR Catolog #53509-138, Rochester, N.Y.), pipet tips for 100–1000 µL pipettor (VWR Catolog #53512-294, Rochester, N.Y.), pipet tips for 2–20 µL and 20–200 µL pipettors (VWR Catolog #53512-260, Rochester, N.Y.), pipets, 10 mL (Becton Dickinson Catalog #7551, Marietta, Ohio), pipets, 2 mL (Becton Dickinson Catalog #7507, Marietta, Ohio, pipets, 5 mL (Becton Dickinson Catalog #7543, Marietta, Ohio), RAW 264.7 Cells (American Type Culture Collection Catalog #TIB-71, Manassas, Va.), test compounds (liquid $CO_2$ hops extract from Hopunion, Yakima, Wash.), tissue culture plates, 96-well (Becton Dickinson Catalog #3075, Franklin Lanes, N.J.), Ultra-pure water (Resistance=18 megaOhm-cm deionized water).

General Procedure—RAW 264.7 cells, obtained from ATCC, were grown in DMEM medium and maintained in log phase growth. The DMEM growth medium was made as follows: 50 mL of heat inactivated FBS and 5 mL of penicillin/streptomycin were added to a 500 mL bottle of DMEM and stored at 4° C. This was warmed to 37° C. in a water bath before use and for best results should be used within three months.

On day one of the experiment, the log phase 264.7 cells were plated at $8 \times 10^4$ cells per well in 0.2 mL growth medium per well in a 96-well tissue culture plate. After 6 to 8 hours post plating, 100 µL of growth medium from each well was removed and replaced with 100 µL fresh medium. A 1.0 mg/mL solution of LPS, which was used to induce the expression of COX-2 in the RAW 264.7 cells, was prepared by dissolving 1.0 mg of LPS in 1 mL DMSO. It was mixed until dissolved and stored at 4° C. Immediately before use, it was thawed at room temperature or in a 37° C. water bath.

On day two of the experiment, the test materials were prepared as 1000× stock in DMSO. For example, if the final concentration of the test material was to be 10 µg/mL, a 10 mg/mL stock was prepared by dissolving 10 mg of the test material in 1 mL of DMSO. Fresh test materials were prepared on day 2 of the experiment. In 1.7 mL microfuge tubes, 1 mL DMEM without FBS was added to obtain test concentrations of 0.05, 0.10, 0.5, and 1.0 µg/mL. 2 µL of the 1000× DMSO stock of the test material was added to the 1 mL of medium without FBS. The tube contained the final concentration of the test material was concentrated 2-fold. The tube was placed in incubator for 10 minutes to equilibrate.

One-hundred mL of medium was removed from each well of the cell plates prepared on day one. One-hundred mL of equilibrated 2×final concentration the test compounds were added to cells and incubated for 90 minutes. LPS in DMEM without FBS was prepared by adding 44 µL of the 1 mg/ml DMSO stock to 10 mL of medium. For each well of cells to be stimulated, 20 µL of LPS (final concentration of LPS is 0.4 µg/mL of LPS) was added. The LPS stimulation was continued for 24 hours, after which the supernatant medium from each well was transferred to a clean microfuge tube for determination of the PGE2 content in the medium.

Determination of COX-1 Enzyme Inhibition by Parthenolide and Andrographolide

The ability of a test material to inhibit COX-1 synthesis of PGE2 was determined essentially as described by Noreen, Y., et al. (J. Nat. Prod. 61, 2–7, 1998).

Equipment—balancer (2400 g, Acculab VI-2400, VWR Catalog #11237-300, Rochester, N.Y.), balancer, analytical, Ohaus Explorer (Ohaus Model #EO1140, Switzerland), biosafety cabinet (Forma Model #F1214, Marietta, Ohio), Freezer, −30° C. (Forma Model #F3797), Freezer, −80° C. Ultralow (Forma Model #F8516, Marietta, Ohio), heated stirring plate (VWR Catalog #33918-262, Rochester, N.Y.), ice maker (Scotsman Model #AFE400A-1A, Fairfax, S.C.), multichannel pipettor, 12-Channel (VWR Catalog #53501-662, Rochester, N.Y.), Multichannel Pipettor, 8-Channel (VWR Catalog #53501-660, Rochester, N.Y.), orbital shaker platform (Scienceware #F37041-0000, Pequannock, N.J.), pH meter (VWR Catalog #33221-010, Rochester, N.Y.), pipet aid (VWR Catalog #53498-103, Rochester, N.Y.), pipettor, 0.5 to 10 µL (VWR Catalog #4000-200, Rochester, N.Y.), pipettor, 100 to 1000 µL (VWR Catalog #4000-208, Rochester, N.Y.), pipettor, 2 to 20 µL (VWR Catalog #4000-202, Rochester, N.Y.), pipettor, 20 to 200 µL (VWR Catalog #4000-204, Rochester, N.Y.), PURELAB Plus Water Polishing System (U.S. Filter, Lowell, Mass.), refrigerator, 4° C. (Forma Model #F3775, Marietta, Ohio), vacuum chamber (Sigma Catalog #Z35, 407-4, St. Louis, Mo.), vortex mixer (VWR Catalog #33994-306, Rochester, N.Y.)

Supplies and Reagents—96-Well, round-bottom plate (Nalge Nunc #267245, Rochester, N.Y.), arachidonic acid (Sigma Catalog #A-3925, St. Louis, Mo.), centrifuge tubes, 15 mL, conical, sterile (VWR Catalog #20171-008, Rochester, N.Y.), COX-1 enzyme (ovine) 40,000 units/mg (Cayman Chemical Catalog #60100, Ann Arbor, Mich.), dimethylsulfoxide (DMSO) (VWR Catalog #5507, Rochester, N.Y.), ethanol 100% (VWR Catalog #MK701908, Rochester, N.Y.), epinephrine (Sigma Catalog #E-4250, St. Louis, Mo.), glutathione (reduced) (Sigma Catalog #G-6529, St. Louis, Mo.), graduated cylinder, 1000 mL (VWR Catalog #24711-364, Rochester, N.Y.), hematin (porcine) (Sigma catalog #H-3281, St. Louis, Mo.), hydrochloric acid (HCl) (VWR Catalog #VW3110-3, Rochester, N.Y.), Kim Wipes (Kimberly Clark Catalog #34256, Roswell, Ga.), microfuge tubes, 1.7 mL (VWR Catalog #20172-698, Rochester, N.Y.), NaOH (Sigma Catalog #S-5881, St. Louis, Mo.), pipet tips for 0.5 to 10 $\mu$L pipettor (VWR Catolog #53509-138, Rochester, N.Y.),pipet tips for 100–1000 $\mu$L pipettor (VWR Catolog #53512-294, Rochester, N.Y.), pipet tips for 2–20 $\mu$L and 20–200 $\mu$L pipettors (VWR Catolog #53512-260, Rochester, N.Y.), prostaglandin E2 (Sigma Catalog #P-5640, St. Louis, Mo.), prostaglandin F2alpha (Sigma Catalog #P-0424, St. Louis, Mo.), stir bar, magnetic (VWR Catalog #58948-193, Rochester, N.Y.), storage bottle, 1000 mL (Corning Catalog #1395-1L, Corning, N.Y.), storage bottle, 100 mL (Corning Catalog #1395-100, Corning, N.Y.), $CO_2$ extract of hops (Hopunion, Yakima, Wash.), Tris-HCl (Sigma Catalog #T-5941, St. Louis, Mo.), ultra-pure water (Resistance=18 megaOhm-cm deionized water).

General Procedure—Oxygen-free 1.0M Tris-HCl buffer (pH 8.0) was prepared as follows. In a 1000 mL beaker, 12.11 g Trizma HCl was dissolved into 900 mL ultra-pure water. The beaker was placed on a stir plate with a stir bar. NaOH was added until the pH reached 8.0. The volume was adjusted to a final volume of 1000 mL and stored in a 1000 mL storage bottle.

The Tris-HCl buffer was placed into a vacuum chamber with the top loosened and the air pump was turned on until the buffer stopped bubbling. The vacuum chamber was then turned off and the storage bottle was tightly covered. This step was repeated each time when oxygen-free Tris-HCl buffer was used.

One mL cofactor solution was prepared by adding 1.3 mg (−) epinephrine, 0.3 mg reduced glutathione and 1.3 mg hematin to 1 mL oxygen free Tris-HCl buffer. The solutions of the test material were prepared as needed. i.e. 10 mg of aspirin was weighed and dissolved into 1 mL DMSO.

Enzymes, i.e. prostaglandin E2 or prostaglandin F2alpha, were dissolved in oxygen free Tris-HCl buffer as follows, i.e. on ice, 6.5 $\mu$L of enzyme at 40,000 units/mL was taken and added to 643.5 $\mu$L of oxygen free Tris-HCl buffer. This enzyme solution is enough for 60 reactions. The COX-1 enzyme solution was prepared as follows: In a 15 mL centrifuge tube, 10 $\mu$L COX-1 enzyme at 40,000 units/mL was added to oxygen free Tris-HCl with 50 $\mu$L of the cofactor solution per reaction. The mixture was incubated on ice for 5 minutes. For 60 reactions, 650 $\mu$l enzyme were added in oxygen free Tris-HCl buffer with 3.25 mL cofactor solution.

Sixty microliters of the enzyme solution were combined with 20 $\mu$l of the test solution in each well of a 96 well plate. Final concentrations of the test solutions were 100, 50, 25, 12.5, 6.25 and 3.12 $\mu$g/mL. The plates were preincubated on ice for 10 minutes. Twenty $\mu$L arachidonic acid (30 $\mu$M) was added and incubated for 15 minutes at 37° C.

Two M HCl was prepared by diluting 12.1 N HCl. in a 100 mL storage bottle. 83.5 mL ultra-pure water was added and then 16.5 mL 12.1 N HCl was added. It was stored in a 100 mL storage bottle and placed in the Biosafty cabinet. The reaction was terminated by adding 10 $\mu$L 2 M HCl. The final solution was used as the supernatant for the $PGE_2$ assay.

Determination of PGE2 Concentration in Medium

The procedure followed was that essentially described by Hamberg, M. and Samuelson, B. (*J. Biol. Chem.* 1971. 246, 6713–6721); however a commercial, nonradioactive procedure was employed.

Equipment—freezer, −30° C. (Forma Model #F3797), heated stirring plate (VWR Catalog #33918-262, Rochester, N.Y.), multichannel pipettor, 12-Channel (VWR Catalog #53501-662, Rochester, N.Y.), orbital shaker platform (Scienceware #F37041-0000, Pequannock, N.J.), Pipet Aid (VWR Catalog #53498-103, Rochester, N.Y.), pipettor, 0.5 to 10 $\mu$L (VWR Catalog #4000-200, Rochester, N.Y.), pipettor, 100 to 1000 $\mu$L (VWR Catalog #4000-208, Rochester, N.Y.), pipettor, 2 to 20 $\mu$L (VWR Catalog #4000-202, Rochester, N.Y.), pipettor, 20 to 200 $\mu$L (VWR Catalog #4000-204, Rochester, N.Y.), plate reader (Bio-tek Instruments Model #Elx800, Winooski, Vt.), PURELAB Plus Water Polishing System (U.S. Filter, Lowell, Mass.), refrigerator, 4° C. (Forma Model #F3775, Marietta, Ohio).

Chemicals, Reagents and Buffers—Prostaglandin $E_2$ EIA Kit-Monoclonal 480-well (Cayman Chemical Catalog #514010, Ann Arbor, Mich.), centrifuge tube, 50 mL, conical, sterile (VWR Catalog #20171-178, Rochester, N.Y.), Dulbecco's Modification of Eagle's Medium (DMEM) (Mediatech Catalog #10-013-CV, Herndon, Va.), graduated cylinder, 100 mL (VWR Catalog #24711-310, Rochester, N.Y.), Kim Wipes (Kimberly Clark Catalog #34256, Roswell, Ga.), microfuge tubes, 1.7 mL (VWR Catalog #20172-698, Rochester, N.Y.), penicillin/streptomycin (Mediatech Catalog #30-001-CI, Herndon, Va.), pipet tips for 0.5 to 10 $\mu$L pipettor (VWR Catolog #53509-138, Rochester, N.Y.), pipet tips for 100–1000 $\mu$L pipettor (VWR Catolog #53512-294, Rochester, N.Y.), pipet tips for 2–20 $\mu$L and 20–200 $\mu$L pipettors (VWR Catolog #53512-260, Rochester, N.Y.), pipets, 25 mL (Becton Dickinson Catalog #7551, Marietta, Ohio), storage bottle, 100 mL (Corning Catalog #1395-100, Corning, N.Y.), storage bottle, 1000 mL (Corning Catalog #1395-1L, Corning, N.Y.), ultra-pure water (Resistance=18 megaOhm-cm deionized water).

General Procedure—EIA Buffer was prepared by diluting the contents of the EIA Buffer Concentrate (vial #4) with 90 ml of Ultra-pure water. Vial #4 was rinsed several times to ensure all crystals had been removed and was then placed into a 100 mL storage bottle and stored at 4° C.

The Wash Buffer was prepared by diluting Wash Buffer Concentrate (vial #5) 1:400 with Ultra-pure water. 0.5 ml/liter of Tween 20 (vial #5a) was then added (using a syringe for accurate measurement). To prepare one liter of Wash Buffer add 2.5 ml Wash Buffer Concentrate, 0.5 ml Tween-20, and 997 ml Ultra-pure water. The solution was stored in a 1 liter storage bottle at 4° C.

The Prostaglandin $E_2$ standard was reconstituted as follows. A 200 $\mu$L pipet tip was equilibrated by repeatedly filling and expelling the tip several times in ethanol. The tip was used to transfer 100 $\mu$L of the $PGE_2$ Standard (vial #3) into a 1.7 mL microfuge tube. 900 $\mu$l Ultra-pure water was added to the tube and stored at 4° C., which was stable for ~6 weeks. The Prostaglandin $E_2$ acetylcholinesterase tracer was reconstituted as follows. 100 $\mu$L $PGE_2$ tracer (vial #2) was mixed with 30 mL of the EIA Buffer in a 50 mL centrifuge tube and stored at 4° C.

The Prostaglandin $E_2$ monoclonal antibody was reconstituted as follows. 100 $\mu$L $PGE_2$ Antibody (vial #1) was mixed with 30 mL of the EIA buffer in a 50 mL centrifuge tube and stored at 4° C.

DMEM with penicillin/streptomycin was prepared by adding 5 mL penicillin/streptomycin into 500 mL DMEM and stored at 4° C.

The plates were set up as follows: Each plate contained a minimum of two blanks (B), two non-specific binding wells (NSB), two maximum binding wells ($B_0$), and an eight point standard curve run in duplicate (S1–S8). Each sample was assayed at a minimum of two dilutions and each dilution was run in duplicate.

The standard was prepared as follows: Eight 1.7 mL microuge tubes were labeled as tubes 1–8. 900 μL DMEM into was added to tube 1 and 500 μL DMEM to tubes 2–8. 100 μL of the $PGE_2$ standard was added to tube 1 and mixed. Five-hundred mL of solution was taken from tube 1 and put into tube 2, and this process was repeated through tube 8.

Fifty mL EIA Buffer and 50 μl DMEM were added into the NSB wells. Fifty μl DMEM was added to the $B_0$ wells. Fifty mL of solution was taken from tube #8 and added to both the lowest standard wells (S8). Fifty mL was taken from tube #7 and added to each of the next two wells. This was continued through to tube #1. (the same pipet tip was used for all 8 of the standards making sure to equilibrate the tip in each new standard by pipeting up and down in that standard. Using a P200, 50 μl of each sample at each dilution was added to the sample wells.

Using a 12 channel pipetor, 50 μl of the Prostaglandin $E_2$ acetylcholinesterase tracer was added to each well except the Total Activity (TA) and the Blank (B) wells. Using the 12 channel pipetor, 50 μl of the Prostaglandin $E_2$ monoclonal antibody was added to each well except the Total Activity (TA), the (NSB), and the Blank (B) wells. The plate was covered with plastic film (item #7) and incubated for 18 hours at 4° C.

The plates were developed as follows: one 100 μL vial of Ellman's Reagent (vial #8) was reconstituted with 50 ml of Ultra-pure water in a 50 mL centrifuge tube. It was protected from light and used the same day. The wells were washed and rinsed five times with Wash Buffer using a 12 channel pipettor. Two-hundred mL of Ellman's Reagent was added to each well using a 12 channel pipettor and 5 μl of Tracer to the total activity (TA) wells was then added to each well using a P10 pipette. The plate was covered with a plastic film and placed on orbital shaker in the dark for 60–90 minutes.

The plate was read in the Bio-tek plate reader at a single wavelength between 405 and 420 nm. Before reading each plate, the bottom was wiped with a Kim wipe. The plate should be read when the absorbance of the wells is in the range of 0.3–0.8 A.U. If the absorbance of the wells exceeded 1.5, they were washed and fresh Ellman' Reagent was added and then redeveloped.

Calculation of Synergy and Combination Index

Synergy between the curcuminoids and andrographolide was assessed using CalcuSyn (BIOSOFT, biosoft.com). This statistical package performs multiple drug dose-effect calculations using the Median Effect methods described by T-C Chou and P. Talaly (Trends Pharmacol. Sci. 4:450–454), hereby incorporated by reference.

Briefly, it correlates the "Dose" and the "Effect" in the simplest possible form: fa/fu=(C/Cm)m, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve. It is estimated by the slope of the median-effect plot.

The median-effect plot is a plot of x=log (C) vs y=log (fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems an r>0.85.

Synergy of test components is quantified using the combination index (CI) parameter. The CI of Chou-Talaly is based on the multiple drug-effect and is derived from enzyme kinetic models (Chou, T.-C. and Talalay, P. (1977) A simple generalized equation for the analysis of multiple inhibitions of Michaelis-Menten kinetic systems. J. Biol. Chem. 252:6438–6442). The equation determines only the additive effect rather than synergism or antagonism. However, synergism is defined as a more than expected additive effect, and antagonism as a less than expected additive effect as proposed by Cho and Talalay in 1983 (Trends Pharmacol. Sci. (1983) 4:450–454). Using the designation of CI=1 as the additive effect, there is obtained for mutually exclusive compounds that have the same mode of action or for mutually non-exclusive drugs that have totally independent modes of action the following relationships: CI<1, =1, and >1 indicating synergism, additivity and antagonism, respectively.

Expected median inhibitory concentrations of the two-component combinations were estimated using the relationship:

$$[1/\text{Expected } IC_{50}] = [A/IC_{50}A] + [B/IC_{50}B]$$

where A=mole fraction of component A in the combination and B=the mole fraction of component B in the combination.

TABLE 3 illustrates the observed and expected median inhibitory concentrations for parthenolide and triptolide for PGE2 production by COX-2 in the RAW 264.7 cell assay. While the expected $IC_{50}$ for the 1:2 combination of parthenolide and triptolide was 0.131 μg/mL, the observed value was 0.032 μg/mL or 4.1-fold greater. This level of difference was unexpected and constitutes a novel finding for the combined COX-2 inhibitory activity of the 1:10 combination of parthenolide and triptolide.

TABLE 3

Observed and Expected Median Inhibitory Concentrations for a Formulation of parthenolide and triptolide

| Components (1:2) | Parthenolide $IC_{50}$ (μg/mL) | Triptolide $IC_{50}$ (μg/mL) | Combination Expected $IC_{50}$ (μg/mL) | Combination Observed $IC_{50}$ (μg/mL) |
|---|---|---|---|---|
| Parthenolide: Triptolide | 0.560 | 0.094 | 0.131 | 0.032 |

Statistical analysis of inhibition of COX-2 production of PGE2 in the RAW 264.7 cell model for the 1:2 combination of parthenolide and triptolide is presented in TABLE 4. The CI for this combination was 0.250, 0.259 and 0.349, respectively, for the $IC_{50}$, $IC_{75}$ and $IC_{90}$. These CI values indicate strong synergy between parthenolide and triptolide over the complete dose-response curve.

TABLE 4

Combination Index for a 1:10 Formulation
of parthenolide and triptolide

| Combination Index | | | |
|---|---|---|---|
| IC50 | IC75 | IC90 | Mean CI |
| 0.250 | 0.295 | 0.349 | 0.298 |

These data are consistent with and support the test results and conclusions performed in the Jurkat cells in which COX-2 protein expression was monitored.

Thus, there has been disclosed a formulation comprising triptolide and parthenolide. The combination formula provides for a synergistic anti-inflammatory effect in response to physical or chemical injury or abnormal immune stimulation due to a biological agent or unknown etiology.

It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, lotion, food or bar manufacturing process as well as vitamins, herbs, flavorings and carriers. Other such changes or modifications would include the use of other herbs or botanical products containing the combinations of the present invention disclosed above.

We claim:

1. A composition for inhibition of inducible cyclooxygenase-2 (COX-2) activity, said composition comprising as a first component an effective amount of a diterpene triepoxide lactone species, and as a second component an effective amount of a sesquiterpene lactone species, wherein the ratio of diterpene triepoxide lactone species to sesquiterpene lactone species is between 100:1 and 1:100.

2. The composition of claim 1 wherein the first and second components are derived from plants or plant extracts.

3. The composition of claim 1 wherein at least one of said first or second component is conjugated with a compound selected from the group consisting of mono- or di-saccharides, amino acids, sulfates, succinate, acetate and glutathione.

4. The composition of claim 1, formulated in a pharmaceutically acceptable carrier.

5. The composition of claim 1, additionally containing one or more members selected from the group consisting of antioxidants, vitamins, minerals, proteins, fats, carbohydrates, glucosamine, chondroitin sulfate and amino-sugars.

6. A composition for inhibition of inducible cyclooxygenase-2 (COX-2) activity, said composition comprising as a first component an effective amount of pharmaceutical grade compound selected from the group consisting of triptolide, triptonide, tripdiolide and tripchlorolide, and as a second component an effective amount of parthenolide, encelin, leucanthin B, enhydrin, melanomdin A, tenulin, confertiflorin, burrodin, psilostachyin A, costunolide, strigol, helenalin, 5-α-hydroxy-dehydrocostuslactone, chlorochrymorin, chrysandiol, chrysartemin A, chrysartemin B, cinerenin, curcolone, cynaropicrin, dehydrocostus lactone, dehydroleucodin, dehydrozaluzanin C, deoxylatucin, eremanthine, eupaformonin, eupaformosanin, eupatolide, furanodienone, heterogorgiolide, lactucin, magnolialide, michelenolide, repin, spirafolide, and zaluzanin C.

7. The composition of claim 6 wherein the first and second components are derived from plants or plant extracts.

8. The composition of claim 6 wherein at least one of said first or second component is conjugated with a compound selected from the group consisting of mono- or di-saccharides, amino acids, sulfates, succinate, acetate and glutathione.

9. The composition of claim 6, formulated in a pharmaceutically acceptable carrier.

10. The composition of claim 6, additionally containing one or more members selected from the group consisting of antioxidants, vitamins, minerals, proteins, fats, carbohydrates, glucosamine, chondrotin sulfate and amino-sugars.

11. A composition for inhibition of inducible cyclooxygenase-2 (COX-2) activity, said composition comprising as a first component an effective amount of pharmaceutical grade triptolide or triptonide, and as a second component an effective amount of a compound selected from the group consisting of parthenolide, encelin, leucanthin B, enhydrin, melapodin A, tenulin, confertiflorin, burrodin, psilostachyin A, costunolide, strigol and helenalin.

12. The composition of claim 11 wherein the first and second components are derived from plants or plant extracts.

13. The composition of claim 11 wherein at least one of said first or second component is conjugated with a compound selected from the group consisting of mono- or di-saccharides, amino acids, sulfates, succinate, acetate and glutathione.

14. The composition of claim 11, formulated in a pharmaceutically acceptable carrier.

15. The composition of claim 11, additionally containing one or more members selected from the group consisting of antioxidants, vitamins, minerals, proteins, fats, carbohydrates, glucosamine, chondrotin sulfate and amino-sugars.

16. A composition for inhibition of inducible cyclooxygenase-2 (COX-2) activity, said composition comprising as a first component an effective amount of pharmaceutical grade triptolide and as a second component an effective amount of a compound selected from the group consisting of parthenolide, encelin, leucanthin B, enhydrin, melapomdin A.

17. The composition of claim 16 wherein the first and second components are derived from plants or plant extracts.

18. The composition of claim 16 wherein at least one of said first or second component is conjugated with a compound selected from the group consisting of mono- or di-saccharides, amino acids, sulfates, succinate, acetate and glutathione.

19. The composition of claim 16, formulated in a pharmaceutically acceptable carrier.

20. The composition of claim 16, additionally containing one or more members selected from the group consisting of antioxidants, vitamins, minerals, proteins, fats, carbohydrates, glucosamine, chondrotin sulfate and amino-sugars.

21. A composition for inhibition of inducible cyclooxygenase-2 (COX-2) activity, said composition comprising as a first component an effective amount of pharmaceutical grade triptolide and as a second component an effective amount of pharmaceutical grade parthenolide.

22. The composition of claim 21 wherein the first and second components are derived from plants or plant extracts.

23. The composition of claim 21 wherein at least one of said first or second component is conjugated with a compound selected from the group consisting of mono- or di-saccharides, amino acids, sulfates, succinate, acetate and gluthathione.

24. The composition of claim 21, formulated in a pharmaceutically acceptable carrier.

25. The composition of claim 21, additionally containing one or more members selected from the group consisting of antioxidants, vitamins, minerals, proteins, fats, carbohydrates, glucosamine, chondrotin sulfate and amino-sugars.

* * * * *